United States Patent [19]

Warren et al.

[11] Patent Number: 5,349,624
[45] Date of Patent: Sep. 20, 1994

[54] SOLID PARTICLE CONTAMINANT DETECTION AND ANALYSIS SYSTEM

[75] Inventors: Jeffrey M. Warren, Herndon, Va.; Richard D. Weller, Laurel, Md.

[73] Assignee: The United States of America as represented by the Secretary of the Navy, Washington, D.C.

[21] Appl. No.: 65,259

[22] Filed: May 21, 1993

[51] Int. Cl.$^5$ .............................................. G21K 3/00
[52] U.S. Cl. ...................................... 378/43; 378/62
[58] Field of Search .................... 378/62, 57, 45, 53, 378/88, 87, 43

[56] References Cited

U.S. PATENT DOCUMENTS 3,860,819  1/1975  Rabodzei et al. ...................... 378/43

Primary Examiner—David P. Porta
Assistant Examiner—Don Wong
Attorney, Agent, or Firm—Jacob Shuster

[57] ABSTRACT

Samples of particulate soil contaminated with solid particles having higher X-ray absorption coefficients than the soil, are irradiated with a microfocused X-ray beam within an analysis zone to produce X-ray images of such samples. By controlling relative scanning and magnifying movements between the samples within the analysis zone and the X-ray beam, image features corresponding to the solid particles in the soil are rendered detectable for measurement purposes and to provide data from which size and distribution of contaminants in the soil are calculated.

10 Claims, 2 Drawing Sheets

1

SOLID PARTICLE CONTAMINANT DETECTION AND ANALYSIS SYSTEM

BACKGROUND OF THE INVENTION

This invention relates generally to the detection and analysis of contaminants in particulate matter, such as soil.

Contaminants such as heavy metal particles in soil are presently detected by methods involving chemical analysis, radiation measurement techniques and microscopic examination. In chemical analysis methods, metal contaminants are dissolved within solutions from which data on the overall percentage of the heavy metal in the soil is obtained by quantitative analysis. In the case of radiation measurement methods, the approximate overall percentage of radiation particles (such as uranium or plutonium) in a soil sample is obtained. The use of electron or optical microscopic examination on the other hand requires prior complete physical separation of the contaminant particles from the soil, involving soil washing or the use of a fluid medium to differentially accelerate movement of the soil and contaminants.

None of the foregoing prior art methods have the capability of providing data on contaminant particle size, geometry and distribution within soil samples. U.S. Pat. No. 4,783,253 to Ayres et al. relates, by way of example, to the separation of particles from soil contaminated by radioactive metals, but relies on prior soil treatment with water thereby foreclosing non-destructive analysis of soil samples to obtain data on size and distribution of contaminant particles therein.

The use of X-ray radiation techniques to detect and analyze contamination of soil or the like is generally known, as disclosed for example in U.S. Pat. Nos. 4,710,946 and 5,058,425 to Hinch et al. and Davis, Jr., et al., respectively. The method disclosed in the Hinch et al. patent is, however, limited to X-ray examination of solid core types of rock samples precluding detection of particles within a small size range (below 1 mm for example). A complete analysis of soil samples with respect to both size and distribution of all contaminant particles therein is therefore not possible through use of the method disclosed in the Hinch et al. patent. Detection and analysis of soil samples with respect to contaminant particle size and distribution is also precluded by the method disclosed in the Davis, Jr. et al. patent, involving treatment of a core of coal to detect its methane storage capacity.

It is therefore an important object of the present invention to provide an improved, non-destructive method of analyzing particulate matter with respect to size and distribution of solid contaminants therein.

In accordance with the foregoing object, the present invention is particularly useful in obtaining data on the size and location of heavy metal contaminants in soil for various purposes, including but not limited to controlling the physical separation of such contaminants from the soil in a more efficient and less costly manner.

SUMMARY OF THE INVENTION

In accordance with the present invention, soil is irradiated by an X-ray beam within an analysis zone for producing X-ray images of soil samples. The X-ray beam is microfocused to approximate a point source so that controlled movement of each soil sample relative to the X-ray beam for sample scanning and image feature magnifying purposes enlarges the X-ray images sufficiently to enable detection and measurement of contrasting image portions corresponding to all of the solid contaminants, including very small particles, from which particle size and location in each of the soil samples may be calculated. Detection of the image portions to be measured is made possible by both image magnification and image contrast as well as possible image enhancement processing on significant differences in X-ray absorption coefficients between the heavy metal contaminant particles and the surrounding particulate silica soil material. The particle size and location type of data so obtained will be useful in effectuating mechanical separation of the contaminant particles from each soil sample following analysis thereof, according to certain embodiments of the invention.

BRIEF DESCRIPTION OF THE DRAWING FIGURES

Other objects, advantages and novel features of the invention will become apparent from the following detailed description of the invention when considered in conjunction with the accompanying drawing wherein.

DETAILED DESCRIPTION OF THE PREFERRED EMBODIMENT

Figure 1:
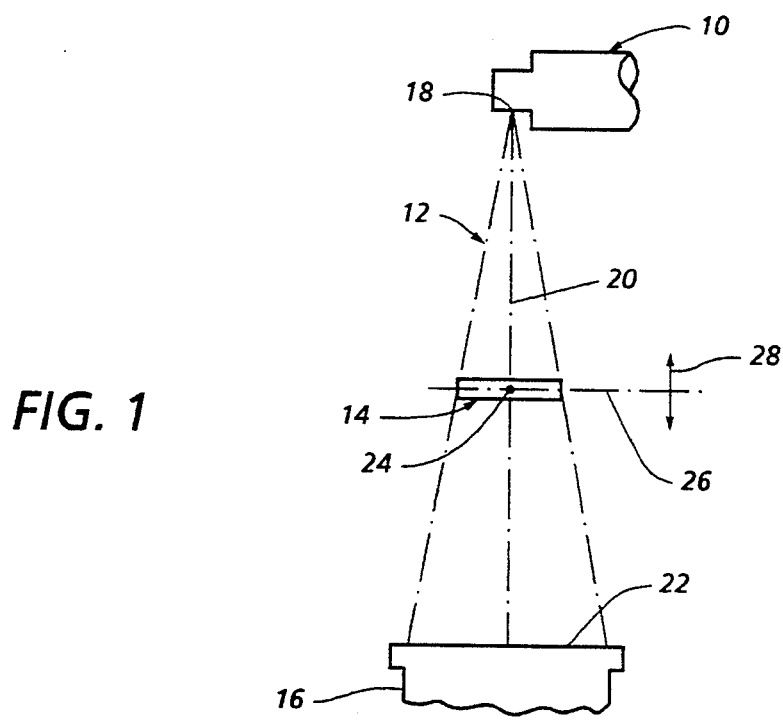
FIG. 1 is a simplified schematic view of an X-ray examination arrangement in accordance with one embodiment of the invention.

Referring now to the drawing in detail, FIG. 1 depicts X-ray tube 10 generating an X-ray beam 12 with sufficient flux and energy to form images of a soil sample 14 pursuant to the present invention. As shown, the soil sample is positioned within an analysis zone between an imaging device 16 and the point source 18 of radiation from X-ray tube 10 along an axis 20 to the image plane 22 of the imaging device. Controlled scanning movement relative to the X-ray beam 12 is imparted to the soil sample 14 along perpendicular scanning axes 24 and 26 intersecting the beam axis 20. Magnification of X-ray images formed on plane 22, on the other hand, is controlled by movement 28 along axis 20 imparted to the soil sample as denoted in FIG. 1. Thus, a controllably scanned and magnified x-ray image of the soil sample is formed at the image plane 22 by generation of the microfocused X-ray beam 12 through equipment associated with X-ray tube 10, such as an X-ray machine operating under a voltage of 80 kv and current of 35 ma. Such a commercially available X-ray machine is marketed, for example, by Feinfocus U.S.A., Inc., as model FSX-100.25.

Figure 2:
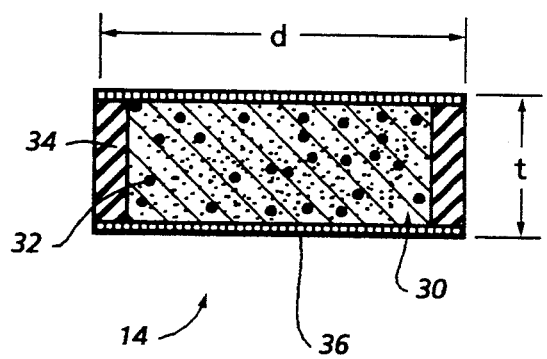
FIG. 2 is an axial plane section view through a soil sample being examined by the arrangement shown in FIG. 1.
Figure 3:
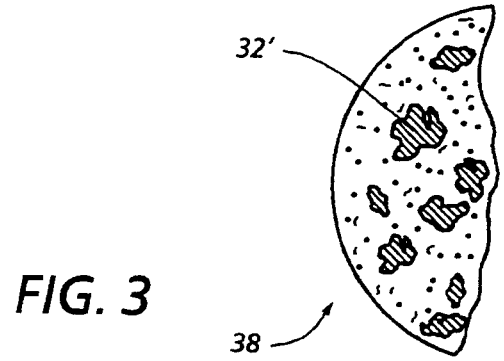
FIG. 3 is an enlarged image of a partial section of the soil sample shown in FIG. 2.

As shown in FIG. 2, the soil sample 14 undergoing examination within the analysis zone between X-ray tube 10 and the image plane 22 is a body of soil 30 contaminated by heavy metal particles 32, including extremely small particles less than one millimeter and as small as 10 microns in size. The contaminated soil body 30 occupies a cylindrical volume formed within a container 34 having circular retainer lids 36 at opposite axial ends. Because the contaminant particles 32 have a significantly higher X-ray absorption coefficient than the low absorption coefficient for the soil alone, the X-ray image 38 of the soil sample as shown in FIG. 3 includes high contrast image feature portions 32' corresponding to the contaminant particles 32. Accordingly, measurement of the size and location of each image portion 32' within its image 38 will provide accurate and useful analysis data from which the size and distribution of the contaminant particles 32 within the body of soil 30 is calculated, based on the geometrical parameters of the soil sample 14 and analysis zone as hereinbefore described with respect to FIG. 1.

According to actual analyses performed pursuant to the present invention, the cylindrical soil samples 14 utilized had a diameter (d) of ½ inch and a thickness (t) between 0.2 and 0.4 inches. The soil in such sample without contamination had an X-ray absorption coefficient between approximately 0.1 and 0.5 $cm^2/g$, which is substantially lower than the X-ray absorption coefficient of the contaminants.

The X-ray image 38 as depicted in FIG. 3 may be recorded on photographic film or captured by electronic means through the imaging device 22. Magnification of the X-ray image is varied to accommodate the size range of the contaminant particles to be detected for measurement purposes, up to a maximum magnification factor of about 250:1 under microfocus X-ray capabilities of presently available X-ray machines. Detection of contaminant particles as small as 10 microns is thereby made possible. Detection of the contaminant particles, as dark spot image portions 32' depicted in FIG. 3, may be further enhanced by electronic image processing.

The scanning movement imparted to the soil sample 14 as hereinbefore described is utilized to obtain measurement data from which the location of the particles 32 may be calculated. Alternatively, a stream of soil may be moved through the analysis zone for intermittent examination of soil samples. The contaminant particle size and location data so obtained may be digitized and fed to automatic computer controlled equipment for subsequent physical separation of the particles. The X-ray images or views may also be captured and measured electronically to provide digitized data on contaminant particle size and location by computer programmed calculation.

Figure 4:
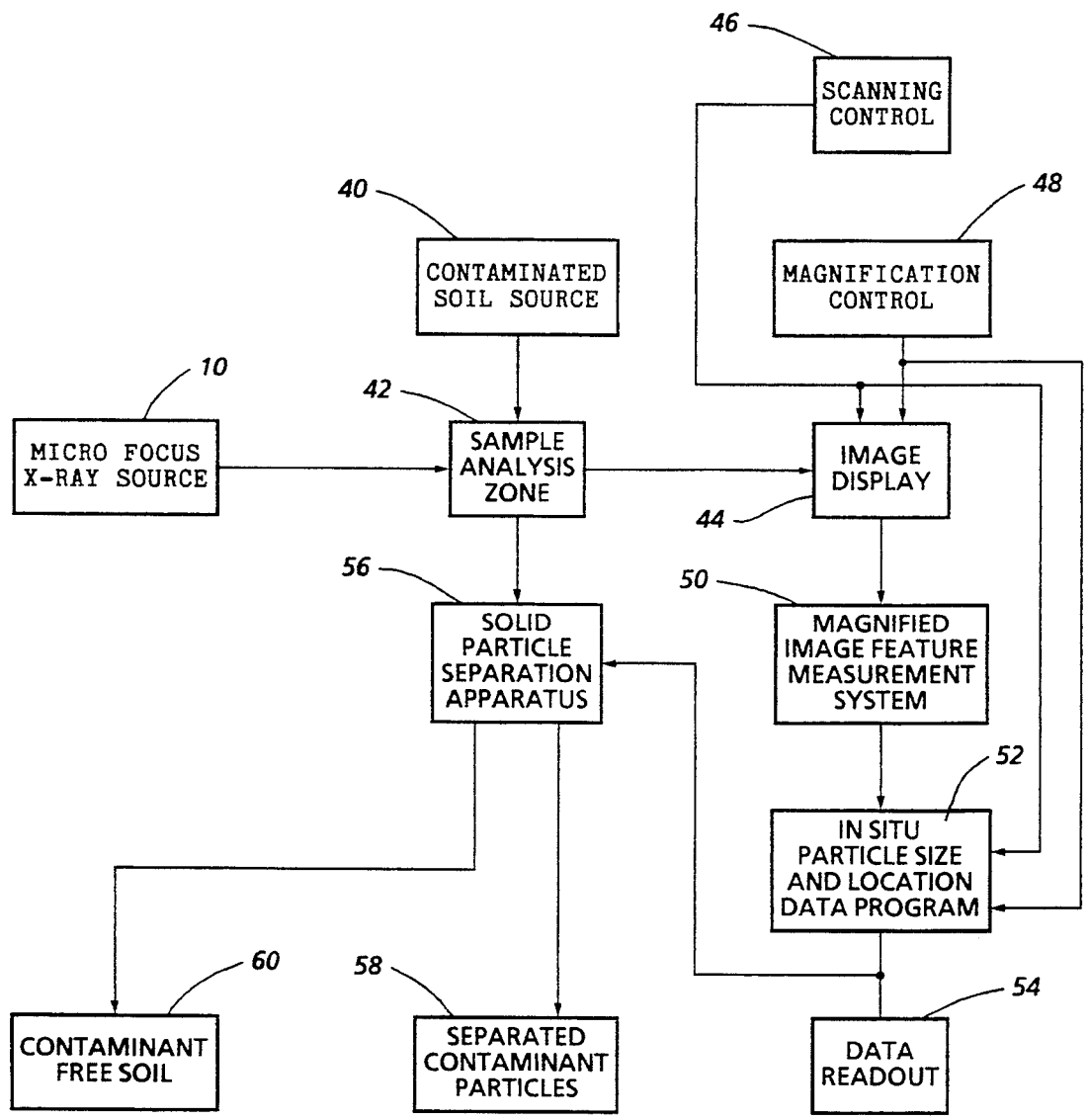
FIG. 4 is a block diagram depicting the method associated with one embodiment of the present invention.

The foregoing sample analysis method is depicted in FIG. 4, wherein block 40 represents a source of contaminated soil fed to a sample analysis zone 42 irradiated by the microfocus X-ray beam from source 10 to produce the image display represented by block 44. Scanning and image magnification control respectively denoted by blocks 46 and 48 is exercised as hereinbefore explained in order to enable measurement of magnified image features through a system denoted by block 50. The measurement data output of the system 50 is then utilized to calculate in situ size and location for contaminant particles through a computer program, as denoted by block 52, in order to obtain a data readout 54.

As also denoted in FIG. 4 by block 56, the size and location data output of program 52 controls operation of particle separation apparatus to which the contaminant soil is fed after passage through the sample analysis zone 42, in order to obtain separated contaminant particles 58 and contaminant-free soil 60. The particle separation apparatus 56 may utilize, for example, an air stream vacuum technique to produce a stream of the contaminant-free soil denoted by block 60. As a result of the foregoing described method, specific in-situ data on size and shape of contaminant particles is produced, and because of soil sample scanning, precise particle location data is provided as the basis for more efficient use of a particle separation technique as well as to drastically reduce the duration and equipment cost for soil sample assessment.

Numerous other modifications and variations of the present invention are possible in light of the foregoing teachings. It is therefore to be understood that within the scope of the appended claims the invention may be practiced otherwise than as specifically described.

What is claimed is:

1. A method for examining particulate matter using X-ray equipment, comprising the steps of: passing a sample of said particulate matter through an analysis zone; directing microfocus X-ray beams generated by the X-ray equipment through said analysis zone to scan said sample and form X-ray images thereof; magnifying said X-ray images to enable detection of feature portions therein corresponding to contaminants within the sample; measuring the magnified X-ray images with respect to size and location of the feature portions therein after said detection thereof; and non-destructively analyzing the particulate matter from the size and location of the feature portions measured as the contaminants.

2. The method of claim 1, including the step of: utilizing the measured size and location of the feature portions of the X-ray images to separate the contaminants from the sample.

3. The method of claim 2 wherein said contaminants include particles less than 1 millimeter in size.

4. The method of claim 3 wherein the contaminants are heavy metals and the particulate matter is soil.

5. The method of claim 1 wherein said contaminants include particles less than 1 millimeter in size.

6. The method of claim 1 wherein the contaminants are solid particles of heavy metal and the particulate matter is soil.

7. A method for analysis of particulate matter contaminated by solid particles therein, comprising the steps of: passing a sample of said particulate matter through an analysis zone, directing a microfocussed X-ray beam through said analysis zone to scan said sample and form X-ray images thereof; magnifying said X-ray images to enable detection of feature portions therein corresponding to said particles; measuring said feature portions of the X-ray images after enlargement by said magnifying thereof; and determining data on size and location of the solid particles in the sample from said measuring of the feature portions to non-destructively perform said analysis of the particulate matter.

8. The method of claim 7 wherein said particulate matter has an X-ray absorption coefficient substantially lower than that of the solid particles therein.

9. The method of claim 8 wherein the X-ray absorption coefficient of the particulate matter is between approximately 0.1 and 0.5 $cm^2/g$.

10. The method of claim 7, including the additional step of: utilizing the determined data on the size and location to separate the solid particles from the particulate matter.

* * * * *